United States Patent [19]

Sugimoto et al.

[11] 4,377,513
[45] Mar. 22, 1983

[54] PROCESS FOR THE PRODUCTION OF HUMAN ERYTHROPOIETIN

[75] Inventors: Kaname Sugimoto; Yasushi Hayashibara, both of Okayama, Japan

[73] Assignees: Ken Hayashibara, Okayama; Shin Ashida, Hyogo, both of Japan

[21] Appl. No.: 291,848

[22] Filed: Aug. 10, 1981

[30] Foreign Application Priority Data

Aug. 25, 1980 [JP] Japan ................. 55-115950

[51] Int. Cl.$^3$ .............. A61K 37/24; C07G 7/00
[52] U.S. Cl. .............. 26/112 R; 424/88; 424/99; 424/95; 424/103; 424/105; 435/68; 435/172; 435/240; 435/848
[58] Field of Search ........... 260/112 R; 424/88, 99, 424/95, 103, 105; 435/68, 172, 240, 848

[56] References Cited

U.S. PATENT DOCUMENTS

| | | |
|---|---|---|
| 3,033,753 | 5/1962 | White et al. ............ 424/101 |
| 3,865,801 | 2/1975 | Chiba et al. ............ 260/112 R |
| 4,198,479 | 4/1980 | Tytell et al. ............ 435/68 |
| 4,254,095 | 3/1981 | Fisher et al. ............ 424/88 X |
| 4,276,282 | 6/1981 | Sugimoto et al. . |
| 4,285,929 | 8/1981 | Sugimoto et al. . |
| 4,296,025 | 10/1981 | Sugimoto ............ 260/112 R |
| 4,303,650 | 12/1981 | Takezawa et al. ........ 260/112 R X |
| 4,328,207 | 5/1982 | Sugimoto ............ 424/85 |

OTHER PUBLICATIONS

*Chemical Abstracts*, 91:86930s (1979).
Miyake, T., et al, "Purification of Human Erythropoietin", *The Journal of Biological Chemistry*, 252, No. 15, pp. 5558-5564 (1977).
Nature, 1961, p. 75, Lowy et al.
Clinica Chimica Acta 13 (1966), pp. 491-497, Lowy et al.
J. Lab & Clinical Med., (1969), pp. 154 $\propto$ 162, Lewis et al.
Chem. Abstracts, vol. 61, 1964, 10920c, Winkert et al.
Chem. Abstracts, vol. 74, 1971, 49756t, Zivny et al.

*Primary Examiner*—Howard E. Schain
*Attorney, Agent, or Firm*—Browdy and Neimark

[57] ABSTRACT

The present invention relates to a process for the production of human erythropoietin.

More precisely, the invention relates to a process for the mass production of human erythropoietin, comprising in vivo multiplication of human lymphoblastoid cells capable of producing human erythropoietin, and human erythropoietin production by the multiplied human lymphoblastoid cells.

The human erythropoietin production according to the present invention is much higher, in terms of human erythropoietin production per cell, than that attained by conventional processes using in vitro tissue culture; thus, human erythropoietin can be used in a sufficient amount for the prevention and treatment of human diseases.

11 Claims, No Drawings

PROCESS FOR THE PRODUCTION OF HUMAN ERYTHROPOIETIN

DETAILED DESCRIPTION OF THE INVENTION

The present invention relates to a process for the production of human erythropoietin.

Human erythropoietin is a hormone essential for erythrocyte formation in human kidney cells.

Although conventional processes for the production of human erythropoietin, such as those by collection from human urine [U.S. Pat. No. 3,865,801], and by tissue culture using human kidney tumor cells [Japan Kokai No. 55,790/79], are known, neither process can realize mass production of human erythropoietin due to the low human erythropoietin content of human urine in the former, and the low human erythropoietin production per cell and low multiplication in the latter.

The present inventors have investigated processes for the mass production of low-cost human erythropoietin. These efforts have resulted in the unexpected finding that human lymphoblastoid cells capable of producing human erythropoietin multiply rapidly and exhibit a higher human erythropoietin production per cell; thus, the cells are suitable for the production of human erythropoietin.

More precisely, the present invention relates to a process for the production of human erythropoietin, characterized in multiplying human lymphoblastoid cells capable of producing human erythropoietin by transplanting said cells to a non-human warm blooded animal body, or alternatively multiplying said cells by allowing said cells to multiply with a device by which the nutrient body fluid of a non-human warm-blooded animal is supplied to said cells, and allowing the cells multiplied by either of the above multiplication procedures to release human erythropoietin.

The process according to the present invention, besides realizing a higher human erythropoietin production, requires no or much less nutrient medium containing expensive serum for cell multiplication, and renders the maintenance of the culture medium during the cell multiplication much easier than in the case of in vitro tissue culture. Particularly, any human lymphoblastoid cells capable of producing human erythropoietin can be multiplied easily while utilizing the nutrient body fluid supplied from a non-human warm-blooded animal body by transplanting said cells to the animal body, or suspending said cells in a diffusion chamber devised to receive the nutrient body fluid, and feeding the animal in the usual way. Also, the process is characterized by stabler and higher cell multiplication, and higher human erythropoietin production per cell.

As to the human lymphoblastoid cells usable in the present invention, any human lymphoblastoid cells can be used so far as they produce human erythropoietin and multiply easily in a non-human warm-blooded animal body. For example, as such cells usable in the present invention there may be used human lymphoblastoid cells in which there has been introduced the human erythropoietin production governing genetic sites of normal human kidney cells or transformed human kidney or liver cells from a patient suffering from kidney carcinoma or liver carcinoma, or human lung carcinoma cells which produce ectopic human erythropoietin. These erythropoietin production governing genetic sites may be introduced by means of cell fusion using polyethylene glycol or Sendai virus, or by genetic recombination techniques using DNA ligase, nuclease and DNA polymerase. Human lymphoblastoid cells which produce ectopic human erythropoietin are also advantageously usable in the present invention. Since the use of such human lymphoblastoid cells results in the formation of easily disaggregatable massive tumor when the cells are transplanted to the animal body, and said massive tumor is hardly contaminated with the host animal cells, the multiplied live human lymphoblastoid cells can be harvested easily.

As to the non-human warm-blooded animals usable in the present invention, any animal can be used so far as the human lymphoblastoid cells multiply therein. For example, poultry such as chicken and pigeon, and mammalians such as dog, cat, monkey, goat, pig, cow, horse, rabbit, guinea pig, rat, hamster, mouse and nude mouse are all advantageously feasible in the invention. Since the transplantation of the human lymphoblastoid cells into the animal elicits undesirable immunoreaction, the use of a newborn or infant animal, or those in the youngest possible stage, for example, egg, embryo or foetus, is desirable. In order to reduce the immunoreaction as much as possible, prior to the transplantation, the animal may be treated with X- or $\gamma$-ray irradiation, about 200-600 rem, or injection of antiserum or immunosuppressive agent prepared according to conventional methods. Since nude mice, used as the non-human warm-blooded animal, exhibit weaker immunoreaction even when in their adulthood, conveniently, any human lymphoblastoid cells can be implanted therein, and multiplied rapidly without such pretreatment.

Stabilized cell multiplication and enhancement of human erythropoietin production can both be carried out by repeated transplantation using combination(s) of different non-human warm-blooded animals; for example, the objectives are attainable first by implanting said cells in hamster and multiplying therein, then by reimplanting in nude mouse. Further, the repeated transplantation may be carried out with animals of the same class or division as well as those of the same species or genus.

As to where the human lymphoblastoid cells are implantable, the cells can be implanted in any sites of the animal so far as the cells multiply therein; for example, in allantoic cavity, or intravenously, intraperitoneally, or subcutaneously.

Besides direct transplantation of the human lymphoblastoid cells to the animal body, any conventional human lymphoblastoid line capable of producing human erythropoietin can be multiplied while utilizing the nutrient body fluid supplied from the animal body by embedding, for example, intraperitoneally, in said animal a conventional diffusion chamber, of any of various shapes and sizes, and equipped with a porous membrane filter, ulta filter or hollow fiber with pore sizes of about $10^{-7}$ to $10^{-5}$ m in diameter which prevents contamination with host cells into the diffusion chamber and allows the animal to supply the cells with its nutrient body fluid. Additionally, the diffusion chamber can be designed, if necessary, so it could be placed, for example, on the host animal, and the body fluid allowed to circulate from the animal body into the chamber, to enable observation of the cell suspension in the chamber through transparent side window(s), equipped on the chamber walls(s), and to enable replacement and exchange with a fresh chamber; cell production per host thereby increases to a further higher level over the period of the animal life without any sacrifice of the host animal.

Furthermore, when such a diffusion chamber is used, since the multiplied human lymphoblastoid cells can be harvested easily and no immunoreaction is elicited due to the absence of direct contact of the human lymphoblastoid cells with the host animal cells, any non-human warm-blooded animal can be used as the host in the present invention without any pretreatment to reduce the immunoreaction.

Feeding of the host animal implanted with the human lymphoblastoid cells can be carried out easily by conventional methods even after the cell transplantation, and no special care is required.

Maximum cell multiplication is attained about 1–20 weeks, generally 1–5 weeks, after the cell transplantation.

According to the present invention, the number of the human lymphoblastoid cells obtained per host ranges from about $10^7$ to $10^{12}$ or more. In other words, the number of the human lymphoblastoid cells transplanted to the animal body increases about $10^2$–$10^7$-fold or more, or about $10^1$–$10^6$ fold or more than that attained by in vitro tissue culture method using nutrient medium; thus, the cells are conveniently usable for human erythropoietin production.

As to the method by which the human lymphoblastoid cells are allowed to release human erythropoietin, any method can be employed so far as the human lymphoblastoid cells obtained by the above mentioned procedure release human erythropoietin thereby. For example, the multiplied human lymphoblastoid cells, obtained by multiplying in ascite in suspension and harvesting from said ascite, or by extracting the massive tumor formed subcutaneously and harvesting after the disaggregation of said massive tumor, are suspended to give a cell concentration of about $10^4$ to $10^8$ cells per ml in a nutrient medium, kept at a temperature of about 20°–40° C., and then incubated at this temperature for an additional one to 50 hours to produce human erythropoietin. In this case, incubation of the cell suspension under a reduced pressure, about 730 mmHg or less, or an oxygen-reduced atmosphere, substituted 10% or more air with other gas(es) such as nitrogen or carbon dioxide gas, enhances further the human erythropoietin production. Also, the objective is effectively attainable by the presence of male hormone such as testosterone, or metal cation such as $Co^{++}$ or $Ni^{++}$.

The human erythropoietin thus obtained can be collected easily by purification and separation techniques using conventional procedures such as salting-out, dialysis, filtration, centrifugation, concentration and lyophilization. If a further purified human erythropoietin preparation is desirable, a preparation of the highest purity can be obtained by the above mentioned techniques in combination with other conventional procedures such as adsorption and desorption with ion exchange, gel fitration, affinity chromatography, isoelectric point fractionation and electrophoresis, thus, a human erythropoietin preparation of a high purity as described in E. Goldwasser et al., The Journal of Biological Chemistry, Vol. 252, pp. 5558–5564 (1977) can be easily obtained.

The human erythropoietin preparation can be advantageously usable alone or in combination with one or more agents for injection, external, internal, or diagnostical administration in the prevention and treatment of human diseases such as anaemia.

The human erythropoietin production in the culture medium was determined by bioassay method using $Fe^{59}$-incorporation as described in P. Marry Coates et al., Nature, No. 4793, pp. 1065–1067 (1961), and expressed by the human erythropoietin unit in which 1 unit of human erythropoietin corresponds to one-tenth of human erythropoietin packed in one vial of the International Standard distributed by the World Health Organization.

Several embodiments of the present invention are disclosed hereinafter.

EXAMPLE 1

Disaggregated human kidney tumor cells, obtained by extracting from a patient suffering from tumor of the kidney and mincing, and a human leukemic lymphoblastoid line Namalwa were suspended together in a vessel with a salt solution containing 140 mM NaCl, 54 mM KCl, 1 mM $NaH_2PO_4$ and 2 mM $CaCl_2$, to give a respective cell concentration of about $10^3$ cells per ml. The ice-chilled cell suspension was mixed with a fresh preparation of the same medium containing UV-irradiation preinactivated Sendai virus, transferred into a 37° C. incubator about five minutes after the mixing, and stirred therein for 30 minutes to effect cell fusion, introducing the human erythropoietin producibility of the human kidney tumor cells into the human leukemic lymphoblastoid line. After cloning the hybridoma cell strain capable of producing human erythropoietin according to conventional methods, the hybridoma cell strain was implanted intraperitoneally in adult nude mice which were then fed in the usual way for five weeks. The resulting massive tumors, about 15 g each, were extracted and disaggregated by mincing and suspending in a physiological saline solution containing trypsin. After washing the cells with Earle's 199 medium (pH 7.2), supplemented with 10 v/v % foetal calf serum, the cells were resuspended in a fresh preparation of the same medium to give a cell concentration of about $10^6$ cells per ml, and incubated at 37° C. for 20 hours under reduced pressure, 700 mmHg, to produce human erythropoietin. Thereafter, the cells were ultrasonicated, and the human erythropoietin in the supernatant was determined. The human erythropoietin production was about 170 units per ml cell suspension.

The control cells, obtained by implanting the human kidney tumor cells in nude mice, feeding the animal in the usual way for five weeks, extracting the resulting subcutaneously formed massive tumors, about 5 g each, and disaggregating the massive tumors, were treated similarly as above. The human erythropoietin production was only about 6 units per ml cell suspension.

EXAMPLE 2

After injection of antiserum, prepared with rabbit according to conventional methods, into newborn hamsters to reduce their immunoreaction, the animals were implanted subcutaneously with a human leukemic lymphoblastoid line JBL wherein the human erythropoietin producibility of the human kidney tumor cells was introduced similarly as in EXAMPLE 1, and then fed in the usual way for five weeks. The resulting massive tumors formed subcutaneously and about 10 g each were extracted and disaggregated by mincing and suspending in physiological saline solution containing collagenase. After washing the cells with Eagle's minimal essential medium (pH 7.2), supplemented with 5 v/v % human serum, the cells were resuspended in a fresh preparation of the same medium to give a cell concentration of about $10^5$ cells per ml, and incubated at 35° C. for 15 hours under an atmosphere in which 20% of air was substituted with carbon dioxide gas, allowing the cells to release human erythropoietin. The human erythropoietin production was about 100 units per ml cell suspension.

The control cells, obtained by implanting the human kidney tumor cells in newborn hamsters, feeding the animals in the usual way for three weeks, extracting the resulting subcutaneously formed massive tumors, about 3 g each, were treated similarly as above. The human erythropoietin production was only about 5 units per ml cell suspension.

EXAMPLE 3

Newborn rats were implanted intraveneously with a human leukemic lymphoblastoid line BALL-1 wherein the human erythropoietin producibility of the human kidney tumor cells was introduced similarly as in EXAMPLE 1, and then fed in the usual way for four weeks. The resulting massive tumors, about 30 g each, were extracted and disaggregated. After washing the cells with RPMI 1640 medium (pH 7.4), supplemented with 10 v/v % foetal calf serum, the cells were resuspended to give a cell concentration of about $10^7$ cells per ml in a fresh preparation of the same medium, and then incubated at 30° C. for 40 hours under an atmosphere wherein 30% of air was substituted with nitrogen gas, allowing the cells to release human erythropoietin. The human erythropoietin production was about 340 units per ml cell suspension.

The control cells, obtained by implanting the human kidney tumor cells in newborn rats, feeding the animals in the usual way for four weeks, extracting the resulting massive tumors, about 5 g each, and disaggregating the massive tumors, were treated similarly as above. The human erythropoietin production was only about 9 units per ml cell suspension.

EXAMPLE 4

After about 400 rem X-ray irradiation of adult mice to reduce their immunoreaction, the animals were implanted subcutaneously with a human leukemic lymphoblastoid line NALL-1 wherein the human erythropoietin producibility of the human kidney tumor cells was introduced similarly as in EXAMPLE 1, and then fed in the usual way for three weeks. The resulting massive tumors formed subcutaneously and about 15 g each were extracted and treated similarly as in EXAMPLE 1 to obtain a cell suspension which was then incubated at 35° C. for 20 hours in a $CO_2$ incubator to produce human erythropoietin. The human erythropoietin production was about 60 units per ml cell suspension.

The control cells, obtained by implanting the human kidney tumor cells in mice, feeding the animals in the usual way for three weeks, extracting the resulting massive tumors, about 5 g each, and disaggregating the massive tumors, were treated similarly as above. The human erythropoietin production was only about 3 units per ml cell suspension.

EXAMPLE 5

A human leukemic lymphoblastoid line TALL-1 wherein the human erythropoietin producibility of the human kidney tumor cells was introduced similarly as in EXAMPLE 1 was suspended in physiological saline solution, and transferred into a plastic cylindrical diffusion chamber, inner volume about 10 ml, and equipped with a membrane filter having a pore size of about 0.5 $\mu$ in diameter. After intraperitoneal embedding of the chamber into an adult rat, the animal was fed in the usual way for four weeks, and the chamber was removed. The human cell density in the chamber attained by the above operation was about $7\times 10^8$ cells per ml which was about $10^2$-fold higher or more than that attained by in vitro cultivation using a $CO_2$ incubator. The human cells thus obtained were treated similarly as in EXAMPLE 3 to produce human erythropoietin. The human erythropoietin production was about 420 units per ml cell suspension.

The control cells, obtained by suspending the human kidney tumor cells in physiological saline solution, transferring the cell suspension into the diffusion chamber, embedding intraperitoneally the chamber in an adult rat, feeding the animal in the usual way for four weeks, and collecting the multiplied human cells (about $10^7$ cells per ml), were treated similarly as above. The human erythropoietin production was only about 12 units per ml cell suspension.

EXAMPLE 6

A human leukemic lymphoblastoid line JBL wherein the human erythropoietin producibility of the human kidney tumor cells was introduced similarly as in EXAMPLE 3 was implanted in allantoic cavities of embryonated eggs which had been preincubated at 37° C. for five days. After incubation of the eggs at this temperature for an additional one week, the multiplied human lymphoblastoid cells were harvested. The cells thus obtained were treated similarly as in EXAMPLE 2 to produce human erythropoietin. The human erythropoietin production was about 130 units per ml cell suspension.

In the control experiment wherein the human kidney tumor cells were implanted similarly as above in allantoic cavities of embryonated eggs, no cell multiplication was noted.

What we claim is:

1. A process for the production of human erythropoietin, comprising
(1) multiplying human lymphoblastoid cells capable of producing human erythropoietin by transplanting said cells to a non-human warm-blooded animal body, and allowing the multiplied human lymphoblastoid cells to release human erythropoietin, or
(2) multiplying human lymphoblastoid cells capable of producing human erythropoietin by allowing said cells to multiply with a device by which the nutrient body fluid of a non-human warm-blooded animal is supplied to said cells, and allowing the multiplied human lymphoblastoid cells to release human erythropoietin.

2. A process as set forth in claim 1, wherein said human lymphoblastoid cells capable of producing human erythropoietin are hybridoma cells derived by means of cell fusion of an established human lymphoblastoid line with human cells capable of producing human erythropoietin.

3. A process as set forth in claim 2, wherein said human cells capable of producing human erythropoietin are human kidney tumor cells.

4. A process as set forth in claim 2, wherein said hybrodoma cells are obtained by cell fusion using Sendai virus.

5. A process as set forth in claim 2, wherein said established human lymphoblastoid line is a human leukemic lymphoblastoid line.

6. A process as set forth in claim 1, wherein said non-human warm-blooded animal is a poultry or a mammalian.

7. A process as set forth in claim 1, wherein said multiplied human lymphoblastoid cells are allowed to release human erythropoietin in the presence of one or more members of the group consisting of male hormone and metal ions.

8. A process as set forth in claim 1, wherein said multiplied human lymphoblastoid cells are allowed to release human erythropoietin under a reduced pressure or a oxygen-reduced atmosphere.

9. A process as set forth in claim 2, wherein said established lymphoblastoid line is Namalwa, BALL-1, NALL-1, TALL-1, or JBL.

10. A process as set forth in claim 1, wherein said non-human warm-blooded animal is selected from the group consisting of chickens, pigeons, dogs, cats, monkeys, goats, pigs, cows, horses, rabbits, guinea pigs, rats, hamsters, mice or new mice.

11. A process as set forth in claim 2, wherein said multiplied human lymphoblastoid cells are allowed to release human erythropoietin in the presence of one or more members of the group consisting of testosterone and $Co^{++}$ and $Ni^{++}$ ions.

* * * * *